United States Patent
Huang et al.

(10) Patent No.: US 9,707,547 B2
(45) Date of Patent: Jul. 18, 2017

(54) OXIDATION CATALYST FOR FURFURAL COMPOUNDS AND APPLYING METHOD THEREOF

(71) Applicant: INDUSTRIAL TECHNOLOGY RESEARCH INSTITUTE, Hsinchu (TW)

(72) Inventors: Ying-Ting Huang, Miaoli County (TW); Jinn-Jong Wong, Hsinchu (TW); Jau-Hong Chen, Chiayi (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/964,872

(22) Filed: Dec. 10, 2015

(65) Prior Publication Data

US 2016/0167027 A1    Jun. 16, 2016

Related U.S. Application Data

(60) Provisional application No. 62/092,276, filed on Dec. 16, 2014.

(30) Foreign Application Priority Data

Oct. 16, 2015 (TW) ............................. 104134011 A

(51) Int. Cl.
| | | |
|---|---|---|
| *C07D 493/00* | (2006.01) | |
| *B01J 27/138* | (2006.01) | |
| *B01J 27/128* | (2006.01) | |
| *C07D 307/68* | (2006.01) | |
| *B01J 27/08* | (2006.01) | |

(Continued)

(52) U.S. Cl.
CPC ............ *B01J 27/138* (2013.01); *B01J 27/08* (2013.01); *B01J 27/128* (2013.01); *B01J 31/04* (2013.01); *C07D 307/46* (2013.01); *C07D 307/48* (2013.01); *C07D 307/68* (2013.01); *B01J 2231/76* (2013.01)

(58) Field of Classification Search
CPC ...................................................... B01J 27/138
USPC ........................................................ 549/464
See application file for complete search history.

(56) References Cited

U.S. PATENT DOCUMENTS

| | | | |
|---|---|---|---|
| 4,211,882 A | 7/1980 | Komatsu et al. | |
| 4,786,753 A | 11/1988 | Partenheimer et al. | |

(Continued)

FOREIGN PATENT DOCUMENTS

| | | | | |
|---|---|---|---|---|
| CN | 104744413 | * | 7/2005 | .......... C07D 307/68 |
| CN | 1942425 A | | 4/2007 | |

(Continued)

OTHER PUBLICATIONS

European Search Report dated Jun. 9, 2016.

(Continued)

*Primary Examiner* — Nizal Chandrakumar
(74) *Attorney, Agent, or Firm* — Rabin & Berdo, P.C.

(57) ABSTRACT

An oxidation catalyst includes a nickel-containing material, a manganese-containing material and a bromine-containing material, wherein the molar number of the element bromine (Br) in the oxidation catalyst to the total molar number of the element nickel (Ni) and the element manganese (Mn) in the oxidation catalyst substantially ranges from 0.01 to 7.5.

4 Claims, 1 Drawing Sheet

(51) Int. Cl.
  *B01J 31/04* (2006.01)
  *C07D 307/46* (2006.01)
  *C07D 307/48* (2006.01)

(56) References Cited

U.S. PATENT DOCUMENTS

| | | | |
|---|---|---|---|
| 5,359,133 | A | 10/1994 | Nazimok et al. |
| 7,348,452 | B2 | 3/2008 | Lavoie |
| 7,700,788 | B2 | 4/2010 | Lilga et al. |
| 7,956,203 | B2 * | 6/2011 | Grushin ............... C07D 307/36 549/488 |
| 8,058,458 | B2 | 11/2011 | Sanborn |
| 8,242,292 | B2 | 8/2012 | Yutaka et al. |
| 8,558,018 | B2 | 10/2013 | Sanborn |
| 8,772,515 | B2 | 7/2014 | Dumesic et al. |
| 8,809,556 | B2 | 8/2014 | Janka et al. |
| 2005/0240055 | A1 | 10/2005 | Lavoie |
| 2009/0156841 | A1 | 6/2009 | Sanborn et al. |
| 2011/0092720 | A1 | 4/2011 | Yutaka et al. |
| 2012/0283452 | A1 | 11/2012 | Munoz De Diego et al. |
| 2012/0302768 | A1 | 11/2012 | Janka et al. |
| 2012/0302769 | A1 | 11/2012 | Janka et al. |
| 2012/0302770 | A1 | 11/2012 | Janka et al. |
| 2012/0302771 | A1 | 11/2012 | Janka et al. |
| 2012/0302772 | A1 | 11/2012 | Shaikh et al. |
| 2012/0302773 | A1 | 11/2012 | Janka et al. |
| 2013/0178617 | A1 | 7/2013 | Raines et al. |
| 2014/0066639 | A1 | 3/2014 | Janka et al. |
| 2014/0256964 | A1 | 9/2014 | Janka et al. |
| 2014/0295508 | A1 | 10/2014 | Yoshikuni et al. |

FOREIGN PATENT DOCUMENTS

| | | |
|---|---|---|
| CN | 101775196 A | 7/2010 |
| CN | 102459214 A | 5/2012 |
| CN | 103842323 A | 6/2014 |
| EP | 2423205 A1 | 2/2012 |
| JP | 2011084540 A | 4/2011 |
| JP | 5252969 B2 | 7/2013 |
| JP | 5550303 B2 | 7/2014 |
| TW | 201202212 A | 1/2012 |
| TW | 201431844 A | 8/2014 |
| TW | 201502116 A | 1/2015 |
| WO | WO 2013-033058 A1 | 3/2013 |
| WO | WO-2013033081 A2 | 3/2013 |
| WO | WO 2014-163500 A1 | 10/2014 |

OTHER PUBLICATIONS

U.S. Appl. No. 14/752,107.
Walt Partenheimer et al. "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts", Adv. Synth. Catal. 2001, 343, 102-111.
Willem P. Dijkman et al., "Enzyme-Catalyzed Oxidation of 5-Hydroxymethylfurfural to Furan-2,5-dicarboxylic Acid", Angew. Chem. Int. Ed. 2014, 53, 6515-6518.
Jiaying Cai et al., "Gold Nanoclusters Confined in a Supercage of Y Zeolite for Aerobic Oxidation of HMF under Mild Conditions", Chem. Eur. J. 2013, 19, 14215-14223.
Hicham Ait Rass et al., "Selective aqueous phase oxidation of 5-hydroxymethylfurfural to 2,5-furandicarboxylic acid over Pt/C catalysts: influence of the base and effect of bismuth promotion", Green Chem., 2013, 15, 2240-2251.
Koteswara Rao Vuyyuru et al., "Oxidation of biomass derived 5-hydroxymethylfurfural using heterogeneous and electrochemical catalysis", Catalysis Today 195 (2012) 144-154.
Taiwanese Office Action dated Oct. 26, 2016.

\* cited by examiner

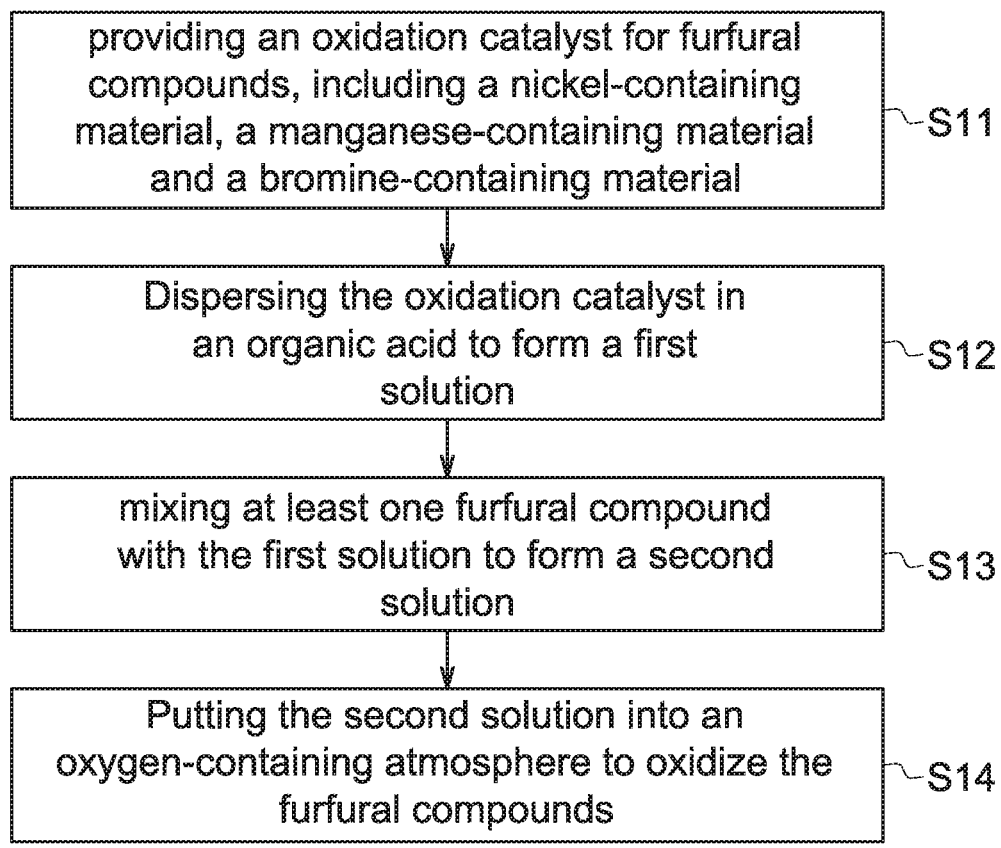

US 9,707,547 B2

OXIDATION CATALYST FOR FURFURAL COMPOUNDS AND APPLYING METHOD THEREOF

This application claims the benefit of U.S. provisional application Ser. No. 62/092,276, filed Dec. 16, 2014 and Taiwan application Serial No. 104134011, filed Oct. 16, 2015, the disclosures of which are incorporated by reference herein in its entirety.

TECHNICAL FIELD

The technical field relates to an oxidation catalyst for forming derivatives of furfural compounds and the applying method thereof.

BACKGROUND 2,5-Furandicarboxylic acid (FDCA), 2,5-diformylfuran (DFF), 5-Formyl-2-furancarboxylic Acid (FFCA) and 5-hydroxymethyl-2-furancarboxylic acid (HMFCA) are the chemical compounds formed by oxidizing 5-Hydroxymethylfurfural (HMF), which is obtained from a hexose (such as fructose or glucose) dehydration. FDCA is one of the symmetrical diacid that can serve as a double-acid monomer reacted with diol compounds in an esterification reaction for forming polyester compounds and elastic materials. Besides, FDCA, which has five-membered rings, can also react with diamine compounds to form nylon. Other derivatives suitable for use as surfactants or plasticizers, or applicable in other new application categories can be also obtained from FDCA.

FDCA typically can be synthesized either under an acidic condition or a basic condition. Although the basic synthesis method may result in higher productivity, it requires expensive precious metal catalysts, such as element platinum (Pt), and produces a large amount of saline wastewater. In contrast, the catalysts used for synthesizing FDCA under acidic condition is cheaper than that used in basic approach, and the acid synthesis solution can be recycled. Such that, using the acidic approach to synthesize FDCA can get more benefits and have more business competition in the commercial market. However, in the acidic synthesis of FDCA, the bromine concentration in the catalysts is high enough (e.g. more than 2000 ppm) to cause corrosion in the reaction system and adversely affect the process for synthesizing FDCA.

Therefore, it is necessary to provide an advanced oxidation catalyst for furfural compounds and the applying method thereof to obviate the problems encountered from the prior art.

SUMMARY

According to one embodiment of the present disclosure, an oxidation catalyst for furfural compounds is provided, wherein the oxidation catalyst includes a nickel-containing material, a manganese-containing material and a bromine-containing material, wherein the molar number of the element bromine (Br) in the oxidation catalyst to the total molar number of the element nickel (Ni) and the element manganese (Mn) in the oxidation catalyst substantially ranges from 0.01 to 7.5.

According to another embodiment, a method for oxidizing furfural compounds is provided, wherein the method includes steps as follows: Firstly, an oxidation catalyst for furfural compounds is provided, wherein the oxidation catalyst includes a nickel-containing material, a manganese-containing material and a bromine-containing material, wherein the molar number of the element Br in the oxidation catalyst to the total molar number of the element Ni and the element Mn in the oxidation catalyst substantially ranges from 0.01 to 7.5. Subsequently, at least one furfural compound is then oxidized in an oxygen-containing atmosphere.

BRIEF DESCRIPTION OF THE DRAWINGS

FIG. 1 is a flow diagram illustrating a method for the oxidation of furfural compounds in accordance with one embodiment of the present disclosure.

DETAILED DESCRIPTION

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

FIG. 1 is a flow diagram illustrating a method for the oxidation of furfural compounds in accordance with one embodiment of the present disclosure. The method includes steps as follows: Firstly, an oxidation catalyst for furfural compounds is provided (see step S11), wherein the oxidation catalyst includes a nickel-containing material, a manganese-containing material and a bromine-containing material. The molar number of the element Br in the oxidation catalyst can be referred to as [Br]; the molar number of the element Ni in the oxidation catalyst can be referred to as [Ni]; and the molar number of the element Mn in the oxidation catalyst can be referred to as [Mn]. The molar number of the element Br ([Br]) to the total molar number ([Ni]+[Mn]) of the element Ni and the element Mn in the oxidation catalyst substantially ranges from 0.01 to 7.5 (i.e. the value of [Br]/([Ni]+[Mn]) substantially ranges from 0.01 to 7.5).

In some embodiments of the present disclosure, the value of [Br]/[Ni] substantially ranges from 0.01 to 20; and the value of [Br]/[Mn] substantially ranges from 0.01 to 20. In some other embodiments of the present disclosure, the value of [Br]/[Ni] substantially ranges from 0.01 to 5; the value of [Br]/[Mn] substantially ranges from 0.01 to 5; and the value of [Br]/([Ni]+[Mn]) substantially ranges from 0.01 to 0.5.

In some yet other embodiments of the present disclosure, the value of [Br]/[Ni] substantially ranges from 0.01 to 15; the value of [Br]/[Mn] substantially ranges from 0.01 to 15; and the value of [Br]/([Ni]+[Mn]) substantially ranges from 0.01 to 5.

In some yet other embodiments of the present disclosure, the value of [Br]/[Ni] substantially ranges from 0.01 to 10; the value of [Br]/[Mn] substantially ranges from 0.01 to 10; and the value of [Br]/([Ni]+[Mn]) substantially ranges from 0.01 to 1.

In some embodiments of the present disclosure, the nickel-containing material can be nickel acetate, nickel bromide, nickel sulfate, nickel chloride, nickel oxalate, nickel carbonate or the arbitrary combinations thereof. The manganese-containing material can be manganese acetate, manganese bromide, manganese sulfate, manganese chloride, manganese oxalate, manganese carbonate or the arbitrary combinations thereof. The bromine-containing material can be nickel bromide, manganese bromide, hydrogen bromide, sodium bromide or the arbitrary combinations thereof.

Next, the oxidation catalyst is dispersed in an organic acid to form a first solution having 0% to 30% water by weight (wt %) (see step S12), wherein the organic acid can be acetic acid, propanoic acid, butyric acid or the arbitrary combinations thereof.

Subsequently, at least one furfural compound is mixed with the first solution to form a second solution having 0% to 30% water by weight (see step S13). In the some embodiments of the present disclosure, the furfural compound can be represented as the following chemical formula:

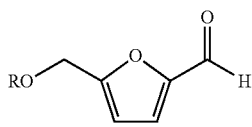

Wherein, R can be H, $CH_3$, $C_2H_5$, $COCH_3$, $COCH_2CH_3$ or $COCH_2CH_2CH_3$. In some embodiments of the present disclosure, the furfural compound is HMF.

The second solution is then put under an oxygen-containing atmosphere to oxidize the furfural compound involved therein (see step S14). Wherein the oxidation reaction is performed at a temperature substantially ranging from 40° C. to 200 t, under a pressure substantially ranging from 1 $kg/cm^2$ to 100 $kg/cm^2$. In some embodiments of the present disclosure, the oxygen-containing atmosphere includes an oxygen gas ($O_2$) with a mole percent (mol %) substantially ranging from 1 to 100 and an assistant-gas selected from a group consisting of nitrogen gas ($N_2$), carbon dioxide ($CO_2$), helium (He), neon (Ne), argon (Ar) and the arbitrary combinations thereof. The oxidation reaction is performed at a temperature substantially ranging from 80° C. to 180 t, under a pressure substantially ranging from 5 $kg/cm^2$ to 30 $kg/cm^2$. In some embodiments of the present disclosure, a multi-stage heating process is applied to adjust the reaction temperatures and pressures in different stage or further adjust the speed of the reaction gas involved in the oxygen-containing atmosphere during the oxidation process of the furfural compounds to achieve higher yields.

The oxidation process of the furfural compound may result in products including FDCA, DFF, FFCA, HMFCA or the arbitrary combinations thereof. Subsequently, purified FDCA, DFF, FFCA, HMFCA or the arbitrary combinations thereof are obtained by filtering, washing, drying, purifying and separating the products of the oxidation process, and the yields thereof are then calculated (see step S14).

Specific embodiments will be described in detail below

Embodiment 1

In the present embodiment, the aforementioned catalyst including element Ni, element Mn and element Br were applied to perform the oxidation process of furfural compound; a comparative embodiment using an oxidation catalyst merely including element Mn and element Br was also provided to perform the oxidation process of furfural compound. The detailed operation thereof is described as follows.

Firstly, 12 grams (g) of nickel acetate, 5.9 g of manganese acetate and 2.02 g of hydrogen bromide were introduced into a 1.0 liter container of a Par reactor having acetic acid disposed therein to form the first solution serving as the oxidation catalyst for the subsequent oxidation reaction. In the present embodiment, the value of [Br]/([Ni]+[Mn]) in the oxidation catalyst was substantially equal to 0.167 ([Br]/([Ni]+[Mn])=0.167). 52 g of HMF was dissolved in a 150 ml acetic acid solution having 2% water by weight and then added into the Par reactor with a feeding speed of 3.5 g per minute to form the second solution. The second solution was then put under an oxygen-containing atmosphere, and oxidation of the furfural compounds involved therein occurred, wherein the reaction temperature was about 150° C., reaction pressure was maintained at about 20 $kg/cm^2$. The temperature was remained in constant for 1 hour and then increased to 180° C., as well remained in constant for another 1 hour. Thereinafter, products were precipitated in the second solution when the second solution was then cooled to room temperature, and the reaction pressure of the Par reactor was released. Purified FDCA, DFF, FFCA, HMFCA or the arbitrary combinations thereof were obtained by filtering, washing, drying, purifying and separating the precipitated products.

Comparative Embodiment 1

Firstly, 5.9 g of manganese acetate and 2.02 g of hydrogen bromide were introduced into a 1.0 liter container of a Par reactor to form an oxidation catalyst for the subsequent oxidation reaction. In the present embodiment, the value of [Br]/[Mn] in the oxidation catalyst compound was substantially equal to 0.5 ([Br]/[Mn]=0.5). 52 g of HMF was dissolved in a 150 ml acetic acid solution having 2% water by weight and then added into the Par reactor with a feeding speed of 3.5 g per minute to form the second solution. The second solution was then put under an oxygen-containing atmosphere, and oxidation of the furfural compounds involved therein occurred, wherein the reaction temperature was about 150° C., reaction pressure was maintained at about 20 $kg/cm^2$. The temperature was remained in constant for 1 hour and then increased to 180° C., as well remained in constant for another 1 hour. Thereinafter, products were precipitated in the second solution when the second solution was then cooled to room temperature, and the reaction pressure of the Par reactor was released. Purified FDCA, DFF, FFCA, HMFCA or the arbitrary combinations thereof was obtained by filtering, washing, drying, purifying and separating the precipitated products.

The detailed results of the oxidation process of the furfural compounds were described in Table 1. The abbreviations of Ni(II)&Mn(II)&Br and Mn(II)&Br(I) respectively represent the oxidation catalyst used for performing the oxidation reaction; Tem and T respectively represent the reaction temperature and the reaction time; and the HMF (wt %) represent the concentration of HMF by weight based on the second solution.

TABLE 1

| Experiment | HMF (wt %) | catalyst | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
|---|---|---|---|---|---|---|---|---|---|---|---|
| Comparative embodiment 1 | 12.5 | Mn(II)&Br | 0.5 | 150/180 | 60/60 | 100 | 53 | 7.1 | 22 | 12 | 1.1 |
| Embodiment 1 | 12.5 | Ni(II)&Mn(II)&Br | 0.167 | 150/180 | 60/60 | 100 | 81 | 38 | 19 | 3.7 | 0.5 |

From the above results, it can be indicated that either the oxidation reaction using the oxidation catalyst including element Ni, element Mn and element Br or the oxidation reaction using the oxidation catalyst merely including element Mn and element Br can result in a mixture of FDCA, DFF, FFCA and HMFCA. However, the yield of the mixture can be significantly improved when the oxidation catalyst including element Ni, element Mn and element Br was applied in the oxidation process of furfural compounds. In the present embodiment, the yield of FDCA was increased from 7.1% to 38%.

In some other embodiment, an oxidation catalyst including element Co, element Mn and element Br can be applied to serve as another comparative embodiment used to verify that the oxidation process of furfural compounds applying the aforementioned catalyst including element Ni, element Mn and element Br has better yield. The detailed operation thereof can be described in the following Embodiments 2-1, 2-2 and 2-3 as well as the Comparative embodiment 2:

Embodiments 2-1, 2-2 and 2-3

Firstly, 5.36 g of nickel acetate, 2.64 g of manganese acetate and 0.9 g of hydrogen bromide were introduced into a 1.0 liter container of a Par reactor having acetic acid disposed therein to form the first solution serving as the oxidation catalyst for the subsequent oxidation reaction. In the present embodiment, the value of [Br]/([Ni]+[Mn]) in the oxidation catalyst was substantially equal to 0.167 ([Br]/([Ni]+[Mn])=0.167). 11.55 g of HMF was dissolved in a 150 ml acetic acid solution having 2% water by weight and then added into the Par reactor to form the second solution. The second solution was then put under an oxygen-containing atmosphere, and oxidation of the furfural compounds involved therein occurred, wherein the reaction temperature was about 150° C. (the reaction temperature in the Embodiments 2-2 and 2-3 was about 180° C.), reaction pressure was maintained at about 20 kg/cm². The temperature was remained in constant for 1 hour and then increased to 180° C., as well remained in constant for another 1 hour. Thereinafter, products were precipitated when the second solution was then cooled to room temperature, and the reaction pressure of the Par reactor was released. Purified FDCA, DFF, FFCA, HMFCA or the arbitrary combinations thereof was obtained by filtering, washing, drying, purifying and separating the precipitated products.

Comparative Embodiment 2

Firstly, 5.36 g of cobalt acetate, 2.64 g of manganese acetate and 0.9 g of hydrogen bromide were introduced into a 1.0 liter container of a Par reactor to form the oxidation catalyst for the subsequent oxidation reaction. 11.55 g of HMF was then dissolved in a 150 ml acetic acid solution having 0.7% water by weight and then added into the Par reactor to form the second solution. The second solution was then put under an oxygen-containing atmosphere, and oxidation of the furfural compounds involved therein occurred, wherein the reaction temperature was about 150° C., reaction pressure was maintained at about 20 kg/cm². The temperature was remained in constant for 1 hour and then increased to 180° C., as well remained in constant for another 1 hour. Thereinafter, products were precipitated when the second solution was then cooled to room temperature, and the reaction pressure of the Par reactor was released. Purified FDCA, DFF, FFCA, HMFCA or the arbitrary combinations thereof was obtained by filtering, washing, drying, purifying and separating the precipitated products.

The detailed results of the oxidation process of the furfural compounds were described in Table 2: Wherein the abbreviations of Ni(If) & Mn(II) & Br and Co(II)&Mn(II)&Br respectively represent the oxidation catalyst used for performing the oxidation reaction; Tem and T respectively represent the reaction temperature and the reaction time; and the HMF (wt %) represent the concentration of HMF by weight based on the second solution.

TABLE 2

| Experiment | HMF (wt %) | catalyst | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
|---|---|---|---|---|---|---|---|---|---|---|---|
| Embodiment 2-1 | 3.3 | Ni(II)&Mn(II)&Br | 0.167 | 150 | 60 | 100 | 96 | 68 | 3.7 | 0 | 0 |
| Embodiment 2-2 | 3.3 | Ni(II)&Mn(II)&Br | 0.167 | 180 | 30 | 100 | 97.3 | 84 | 1.1 | 0 | 0 |
| Embodiment 2-3 | 3.3 | Ni(II)&Mn(II)&Br | 0.167 | 180 | 20 | 100 | 96.4 | 89.3 | 0 | 0 | 0 |
| Comparative embodiment 2 | 3.3 | Co(II)&Mn(II)&Br | 0.167* | 180 | 60 | 100 | 98 | 60 | 2.18 | 0 | 0 |

*[Br]/([Co] + [Mn])

From the above results, it can be indicated that the mixture of FDCA, DFF, FFCA and HMFCA obtained from the oxidation reaction using the oxidation catalyst including element Ni, element Mn and element Br was significantly greater than that obtained from the oxidation reaction using the oxidation catalyst merely including element Co, element Mn and element Br. In the Embodiments 2-1, 2-2 and 2-3, the yield of FDCA was increased at least 10%.

In some embodiments of the present disclosure, the concentration of the HMF may be increased to maximize the efficiency of the oxidation process. The detailed operation thereof can be described in the following Embodiments 3-1 and 3-2. Since the operation method and the parameters of the Embodiments 3-1 and 3-2 were similar to that of the Embodiments 2-1, 2-2 and 2-3 except that the concentration of the HMF, thus the detailed steps for implementing the Embodiments 3-1 and 3-2 will not be redundantly described. In the Embodiments 3-1 and 3-2, the concentration of the HMF was increased to 6%.

The detailed results of the Embodiments 3-1 and 3-2 were described in Table 3: Wherein the abbreviations of Ni(II) & Mn(II) & Br represent the oxidation catalyst used for performing the oxidation reaction; Tem and T respectively represent the reaction temperature and the reaction time; and the HMF (wt %) represent the concentration of HMF by weight based on the second solution.

therein occurred, wherein the reaction temperature was about 80° C., 100° C., and 150° C. and the reaction time was 30 minutes, 30 minutes and 90 minutes respectively. The reaction pressure was maintained at about 20 kg/cm$^2$. Thereinafter, products were precipitated when the second solution was then cooled to room temperature, and the reaction pressure of the Par reactor was released. Purified FDCA, DFF, FFCA, HMFCA or the arbitrary combinations thereof was obtained by filtering, washing, drying, purifying and separating the precipitated products.

Embodiments 4-2 and 4-3

Since the operation method and the parameters of the Embodiments 4-2 and 4-3 were similar to that of the Embodiment 4-1 except that the reaction time and the molar number of the element Ni, element Mn and element Br in the oxidation catalyst was different, thus the detailed steps for

TABLE 3

| Experiment | HMF (wt %) | catalyst | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
| --- | --- | --- | --- | --- | --- | --- | --- | --- | --- | --- | --- |
| Embodiment 3-1 | 6.6 | Ni(II)&Mn(II)&Br | 0.167 | 150 | 60 | 100 | 93 | 64.1 | 3.6 | 0 | 0 |
| Embodiment 3-2 | 6.6 | Ni(II)&Mn(II)&Br | 0.167 | 150/180 | 20/20 | 100 | 95 | 78.2 | 0.7 | 0 | 0 |

In some embodiments of the present disclosure, the molar number of the element Ni, element Mn and element Br in the oxidation catalyst may be varied while the concentration of the HMF was increased to find the parameters in different contexts. The detailed operation thereof can be described in the following Embodiments 4-1, 4-2 and 4-3:

implementing the Embodiments 4-2 and 4-3 will not be redundantly described. In the Embodiments 4-2 and 4-3, the value of [Br]/([Ni]+[Mn]) in the oxidation catalyst was substantially equal to 0.33 ([Br]/([Ni]+[Mn])=0.33).

The detailed results of the Embodiments 4-1, 4-2 and 4-3 were described in Table 4:

TABLE 4

| Experiment | HMF (wt %) | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
| --- | --- | --- | --- | --- | --- | --- | --- | --- | --- | --- |
| Embodiment 4-1 | 12.5 | 0.167 | 80/100/150 | 30/30/90 | 100 | 93 | 51.6 | 9.6 | 0.4 | 0 |
| Embodiment 4-2 | 12.5 | 0.33 | 80/100/150 | 30/30/90 | 100 | 89 | 53.2 | 10 | 0.4 | 0 |
| Embodiment 4-3 | 12.5 | 0.33 | 80/100/150 | 30/60/90 | 100 | 92 | 61.4 | 5.6 | 0 | 0.1 |

Embodiment 4-1

Firstly, 12 g of nickel acetate, 5.9 g of manganese acetate and 2.02 g of hydrogen bromide were introduced into a 1.0 liter container of a Par reactor having acetic acid disposed therein to form the first solution serving as the oxidation catalyst for the subsequent oxidation reaction. In the present embodiment, the value of [Br]/([Ni]+[Mn]) in the oxidation catalyst was substantially equal to 0.167 ([Br]/([Ni]+[Mn]) =0.167). 11.55 g of HMF was dissolved in a 150 ml acetic acid solution having 1.8% water by weight and then added into the Par reactor form the second solution. The second solution was then put under an oxygen-containing atmosphere, and oxidation of the furfural compounds involved In some embodiments of the present disclosure, the content of the element Br in the oxidation catalyst may be independently varied to find the parameter of the oxidation catalyst. The detailed operation of the oxidation process applying the oxidation catalyst with various concentrations of the element Br can be described in the following Embodiments 5-1 to 5-8:

Since the operation method and the parameters of the Embodiments 5-1 to 5-8 were similar to that of the Embodiments 2-1, 2-2 and 2-3 except that the content of the element Br in the oxidation catalyst was different, thus the detailed steps for implementing the Embodiments 5-1 to 5-8 will not be redundantly described. In addition, the reaction pressure applied in the Embodiments 5-1 to 5-8 may be maintained at about 30 kg/cm².

The detailed results of the Embodiments 5-1 to 5-8 were described in Table 5: Wherein the abbreviation of Br (ppm) represents the content of the element Br in the oxidation catalyst.

corrosion of the reaction system caused by element Br without affecting the yield of the mixture of FDCA, DFF, FFCA and HMFCA. In the Embodiments 5-1 to 5-8, the content of the element Br substantially ranges from 20 ppm to 1100 ppm.

In some embodiments of the present disclosure, the content of the element Mn in the oxidation catalyst may be

TABLE 5

| Experiment | HMF (wt %) | Br(ppm) | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
|---|---|---|---|---|---|---|---|---|---|---|---|
| Embodiment 5-1 | 3.3 | 0 | 0 | 180 | 20 | 81 | — | 0 | 0 | 32 | 0.4 |
| Embodiment 5-2 | 3.3 | 11 | 0.00167 | 180 | 20 | 87 | — | 0.24 | 2.9 | 28 | 2.3 |
| Embodiment 5-3 | 3.3 | 22 | 0.0033 | 180 | 20 | 88 | 99.9 | 76.6 | 0.1 | 0 | 0 |
| Embodiment 5-4 | 3.3 | 115 | 0.0167 | 180 | 20 | 95 | 99.3 | 75.9 | 0.7 | 0 | 0.1 |
| Embodiment 5-5 | 3.3 | 231 | 0.033 | 180 | 20 | 100 | 96.7 | 72.5 | 0 | 0 | 0 |
| Embodiment 5-6 | 3.3 | 694 | 0.1 | 180 | 20 | 100 | 97.2 | 83.9 | 0 | 0 | 0 |
| Embodiment 5-7 | 3.3 | 1080 | 0.167 | 180 | 20 | 100 | 96.4 | 89.3 | 0 | 0 | 0 |
| Embodiment 5-8 | 3.3 | 1623 | 0.23 | 180 | 20 | 100 | 96.0 | 68.2 | 0 | 0 | 0 |

From the above results, it can be indicated that the yield of the mixture of FDCA, DFF, FFCA and HMFCA can be increased as the content of the element Br in the oxidation catalyst was increased. However, the effect of changing the molar number of the element Br in the oxidation catalyst was not obvious, and exceptions may exist. The yield of the mixture of FDCA, DFF, FFCA and HMFCA can be remained at a level of 76.7%, and the yield of FDCA can reach 76.6%, when the content of the element Br in the oxidation catalyst was reduced to 22 ppm (see the results of the Embodiment 5-3 in Table 5). When the content of the element Br in the oxidation catalyst was increased to 1080 ppm, the highest yield of the mixture of FDCA, DFF, FFCA and HMFCA, which reached about 89.3%, was obtained (see the results of the Embodiment 5-7 in Table 5). The yield of the mixture of FDCA, DFF, FFCA and HMFCA can be decreased to 68.2% or a lower level, when the content of the element Br in the oxidation catalyst exceeded 1080 ppm (see the results of the Embodiment 5-8 in Table 5).

Therefore, an oxidation catalyst having a lower content of the element Br therein can be obtained, to prevent the independently varied to find the parameter of the oxidation catalyst. The detailed operation of the oxidation process applying the oxidation catalyst with various concentrations of the element Mn can be described in the following Embodiments 6-1 to 6-6:

Since the operation method and the parameters of the Embodiments 6-1 to 6-6 were similar to that of the Embodiments 2-1, 2-2 and 2-3 except that the content of the element Mn in the oxidation catalyst was different, thus the detailed steps for implementing the Embodiments 6-1 to 6-6 will not be redundantly described. In addition, the reaction pressure applied in the Embodiments 6-1 to 6-6 may be maintained at about 30 kg/cm².

The detailed results of the Embodiments 6-1 to 6-6 were described in Table 6: Wherein the abbreviation of Mn (ppm) represents the content of the element Mn in the oxidation catalyst.

TABLE 6

| Experiment | HMF (wt %) | Mn (ppm) | [Br]/[Ni] | [Br]/[Mn] | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
|---|---|---|---|---|---|---|---|---|---|---|---|---|---|
| Embodiment 6-1 | 3.3 | 0 | 0.25 | — | 0.25 | 180 | 20 | 90 | — | 2.5 | 1.7 | 11 | 0.6 |
| Embodiment 6-2 | 3.3 | 158 | 0.25 | 5 | 0.24 | 180 | 20 | 100 | 96.1 | 40.1 | 0 | 0 | 0 |
| Embodiment 6-3 | 3.3 | 785 | 0.25 | 1 | 0.2 | 180 | 20 | 100 | 97.2 | 67.9 | 0 | 0 | 0 |
| Embodiment 6-4 | 3.3 | 1586 | 0.25 | 0.5 | 0.17 | 180 | 20 | 100 | 96.4 | 89.3 | 0 | 0 | 0 |
| Embodiment 6-5 | 3.3 | 3082 | 0.25 | 0.25 | 0.13 | 180 | 20 | 100 | 91.5 | 64.9 | 0 | 0 | 0 |
| Embodiment 6-6 | 3.3 | 4628 | 0.25 | 0.167 | 0.1 | 180 | 20 | 100 | 91.5 | 72.2 | 0 | 0 | 0 |

From the above results, it can be indicated that the yield of the mixture of FDCA, DFF, FFCA and HMFCA can be increased as the content of the element Mn in the oxidation catalyst was increased. However, exceptions may exist. The yield of the mixture of FDCA, DFF, FFCA and HMFCA can be remained at a level of 40.1%, when the content of the element Mn in the oxidation catalyst was reduced to 158 ppm (see the results of the Embodiment 6-2 in Table 6). When the content of the element Mn in the oxidation catalyst was increased to 1586 ppm, the highest yield of the mixture of DFF, FFCA and HMFCA, about 89.3%, was obtained (see the results of the Embodiment 6-4 in Table 6). In the Embodiments 6-1 to 6-6, the content of the element Mn substantially ranges from 500 ppm to 5000 ppm.

In some embodiments of the present disclosure, the content of the element Ni in the oxidation catalyst may be independently varied to find the parameter of the oxidation catalyst. The detailed operation of the oxidation process applying the oxidation catalyst with various concentrations of the element Ni can be described in the following Embodiments 7-1 to 7-8.

Since the operation method and the parameters of the Embodiments 7-1 to 7-8 were similar to that of the Embodiments 2-1, 2-2 and 2-3 except that the content of the element Ni in the oxidation catalyst was different, thus the detailed steps for implementing the Embodiments 7-1 to 7-8 will not be redundantly described. In addition, the reaction pressure applied in the Embodiments 7-1 to 7-8 may be maintained at about 30 kg/cm$^2$.

The detailed results of the Embodiments 7-1 to 7-8 were described in Table 7: Wherein the abbreviation of Ni (ppm) represents the content of the element Ni in the oxidation catalyst.

the results of the Embodiment 7-5 in Table 7). In the Embodiments 7-1 to 7-8, the content of the element Ni substantially ranges from 100 ppm to 12000 ppm.

In some embodiments of the present disclosure the oxidation catalyst may include a magnesium-containing material to improve the yield. The molar number of the element magnesium (Mg) in the oxidation catalyst can be referred to as [Mg]. The value of [Br]/[Mg] substantially ranges from 0.01 to 20; ranges from 0.01 to 7.5; and ranges from 0.01 to 5. The magnesium-containing material can be magnesium acetate, magnesium bromide, magnesium sulfate, magnesium chloride, magnesium oxalate, magnesium carbonate or the arbitrary combinations thereof.

The detailed operation of the oxidation process applying the oxidation catalyst with various concentrations of the element Mg can be described in the following Embodiments 8-1 to 8-2.

Since the operation method and the parameters of the Embodiments 8-1 to 8-2 were similar to that of the Embodiments 2-1, 2-2 and 2-3 except that extra amount of the element Mg in the oxidation catalyst was introduced to the catalyst system in each case, thus the detailed steps for

TABLE 7

| Experiment | HMF (wt %) | Ni (ppm) | [Br]/ [Ni] | [Br]/ [Mn] | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
|---|---|---|---|---|---|---|---|---|---|---|---|---|---|
| Embodiment 7-1 | 3.3 | 0 | — | 0.5 | 0.500 | 180 | 20 | 100 | 95.8 | 54.8 | 1.5 | 0 | 0.1 |
| Embodiment 7-2 | 3.3 | 171 | 5 | 0.5 | 0.455 | 180 | 20 | 100 | 94.2 | 64.8 | 0.4 | 0 | 0 |
| Embodiment 7-3 | 3.3 | 857 | 1 | 0.5 | 0.333 | 180 | 20 | 100 | 96.6 | 68.4 | 0 | 0 | 0 |
| Embodiment 7-4 | 3.3 | 1708 | 0.5 | 0.5 | 0.250 | 180 | 20 | 100 | 93.6 | 70.4 | 1.1 | 0 | 0 |
| Embodiment 7-5 | 3.3 | 3388 | 0.25 | 0.5 | 0.167 | 180 | 20 | 100 | 96.4 | 89.3 | 0 | 0 | 0 |
| Embodiment 7-6 | 3.3 | 5052 | 0.167 | 0.5 | 0.125 | 180 | 20 | 100 | 93.6 | 78.3 | 0.7 | 0 | 0 |
| Embodiment 7-7 | 3.3 | 8298 | 0.1 | 0.5 | 0.083 | 180 | 20 | 89 | 95.9 | 80.1 | 0.2 | 0 | 0 |
| Embodiment 7-8 | 3.3 | 11219 | 0.071 | 0.5 | 0.063 | 180 | 20 | 89 | 97.1 | 74.4 | 0.3 | 0 | 0 |

From the above results, it can be indicated that the yield of the mixture of FDCA, DFF, FFCA and HMFCA can be increased as the content of the element Ni in the oxidation catalyst was increased. However, exceptions may exist. The yield of the mixture of FDCA, DFF, FFCA and HMFCA can be remained at a level of 65.2%, when the content of the element Ni in the oxidation catalyst was reduced to 171 ppm (see the results of the Embodiment 7-2 in Table 7). When the content of the element Ni in the oxidation catalyst was increased to 3388 ppm, the highest yield of the mixture of DFF, FFCA and HMFCA, about 89.3%, was obtained (see implementing the Embodiments 8-1 to 8-2 will not be redundantly described. In addition, the reaction pressure applied in the Embodiments 8-1 to 8-2 may be maintained at about 30 kg/cm$^2$. The contents of the element Mg in the oxidation catalyst applied by the Embodiments 8-1 to 8-2 were respectively about 244 ppm and 480 ppm.

The detailed results of the Embodiments 8-1 to 8-2 were described in Table 8: Wherein the abbreviation of Mg (ppm) represents the content of the element Mg in the oxidation catalyst.

TABLE 8

| Experiment | HMF (wt %) | Mg (ppm) | [Br]/[Mg] | [Br]/[Ni] | [Br]/[Mn] | [Br]/([Ni] + [Mn]) | Tem (° C.) | T (min) | HMF conversion efficiency (%) | FDCA purity (%) | FDCA yield (%) | FFCA yield (%) | DFF yield (%) | HMFCA yield (%) |
|---|---|---|---|---|---|---|---|---|---|---|---|---|---|---|
| Embodiment 8-1 | 3.3 | 244 | 1.35 | 0.125 | 0.5 | 0.167 | 180 | 20 | 100 | 98 | 87 | 0.56 | 0 | 0 |
| Embodiment 8-2 | 5 | 480 | 0.68 | 0.125 | 0.5 | 0.167 | 180 | 20 | 100 | 97.5 | 79.5 | 0 | 0 | 0 |

From the above results, it can be indicated that the yield of the mixture of FDCA, DFF, FFCA and HMFCA can reach 87.56%, when the concentration of the HMF was about 3.3%, and the content of the element Mg in the oxidation catalyst was about 244 ppm (see the results of the Embodiment 8-1 in Table 8), and the yield of the mixture of FDCA, DFF, FFCA and HMFCA can reach 79.5%, when the concentration of the HMF was about 5%, and the content of the element Mg in the oxidation catalyst was about 480 ppm (see the results of the Embodiment 8-2 in Table 8).

According to the aforementioned embodiments, an oxidation catalyst for furfural compounds and a method for applying the oxidation catalyst to oxidize the furfural compounds are provided. An oxidation catalyst including a nickel-containing material, a manganese-containing material and a bromine-containing material is provided to substitute the conventional precious metal catalysts for oxidation of furfural compounds. In some embodiments of the present disclosure, the bromine concentration of the oxidation catalyst is controlled in a certain range to prevent corrosion of the reaction system which may interrupt the oxidation process. Thereby, the cost of the oxidation process can be decreased and the yield of the oxidation process can be improved.

It will be apparent to those skilled in the art that various modifications and variations can be made to the disclosed embodiments. It is intended that the specification and examples is considered as exemplary only, with a true scope of the disclosure being indicated by the following claims and their equivalents.

What is claimed is:

1. A catalyst for oxidizing 5-Hydroxymethylfurfural (HMF) in an acetic acid solution, comprising:
   nickel acetate;
   manganese acetate; and
   hydrogen bromide;
   wherein the molar number of an element bromine (Br) in the catalyst to the total molar number of an element nickel (Ni) and an element manganese (Mn) in the catalyst ranges from 0.01 to 0.5, and
   wherein, referring to the molar number of the element Br in the catalyst as [Br], the molar number of the element Ni in the catalyst as [Ni], and the molar number of the element Mn in the catalyst as [Mn], the value of [Br]/[Ni] ranges from 0.01 to 5, and the value of [Br]/[Mn] ranges from 0.167 to 5.

2. The catalyst according to claim 1, further comprising a magnesium-containing material, wherein referring to the molar number of an element Mg in the catalyst as [Mg], the value of [Br]/[Mg] ranges from 0.01 to 20.

3. The catalyst according to claim 2, wherein the value of [Br]/[Mg] ranges from 0.01 to 5.

4. The catalyst according to claim 2, wherein the magnesium-containing material is selected from a group consisting of magnesium acetate, magnesium bromide, magnesium sulfate, magnesium chloride, magnesium oxalate, magnesium carbonate and arbitrary combinations thereof.

* * * * *